United States Patent
Huang et al.

(10) Patent No.: US 11,097,158 B2
(45) Date of Patent: Aug. 24, 2021

(54) GAIT TRAINING MACHINE AND METHOD OF USING SAME

(71) Applicant: HIWIN TECHNOLOGIES CORP., Taichung (TW)

(72) Inventors: Chao-Ju Huang, Taichung (TW); Jia-Ming Shiu, Taichung (TW); Yi-Jing Wu, Taichung (TW)

(73) Assignee: HIWIN TECHNOLOGIES CORP., Taichung (TW)

( * ) Notice: Subject to any disclaimer, the term of this patent is extended or adjusted under 35 U.S.C. 154(b) by 203 days.

(21) Appl. No.: 16/553,896

(22) Filed: Aug. 28, 2019

(65) Prior Publication Data

US 2021/0060383 A1  Mar. 4, 2021

(51) Int. Cl.
| | |
|---|---|
| A63B 24/00 | (2006.01) |
| A61B 5/11 | (2006.01) |
| A63B 71/06 | (2006.01) |
| A63B 21/00 | (2006.01) |
| A63B 22/00 | (2006.01) |
| A61H 3/00 | (2006.01) |
| A61H 1/02 | (2006.01) |

(52) U.S. Cl.
CPC .......... *A63B 24/0062* (2013.01); *A61B 5/112* (2013.01); *A63B 21/4034* (2015.10); *A63B 22/0056* (2013.01); *A63B 71/0686* (2013.01); *A61H 1/0262* (2013.01); *A61H 3/00* (2013.01); *A63B 2071/0675* (2013.01); *A63B 2220/56* (2013.01); *A63B 2230/01* (2013.01)

(58) Field of Classification Search
None
See application file for complete search history.

(56) References Cited

U.S. PATENT DOCUMENTS

| | | | |
|---|---|---|---|
| 7,266,424 B2 | 9/2007 | Lee et al. | |
| 8,177,688 B2 * | 5/2012 | Burnfield | ........... A63B 21/4015 482/7 |

(Continued)

FOREIGN PATENT DOCUMENTS

JP    2018102842 A  *  7/2018

OTHER PUBLICATIONS

EPO Machine translation of JP 2018102842A (40 pages). (Year: 2018).*

*Primary Examiner* — Joshua Lee
(74) *Attorney, Agent, or Firm* — Muncy, Geissler, Olds & Lowe, P.C.

(57) ABSTRACT

A gait training machine includes a base, a driving module including a driving circuit, a motor and two moving platforms, a sensor module including a left pedal, a right pedal, a plurality of pressure sensors and a position sensor, a controller electrically connected to the driving circuit, each pressure sensor and the position sensor and a signal processing module disposed in the controller and including a gait detecting unit and a gait determining unit with a center-of-gravity calculation logic and a gait determining logic stored therein. Using the above gait training machine to determine whether the bearing weight of the left pedal and the right pedal is correct, and whether the center-of-gravity position is correct, so that the user can know the ankle joint movement and the center-of-gravity during gait training to adjust the health gait posture.

10 Claims, 10 Drawing Sheets

(56) References Cited

U.S. PATENT DOCUMENTS

| | | | | |
|---|---|---|---|---|
| 8,613,691 | B2* | 12/2013 | Bosecker | A61H 1/005 |
| | | | | 482/54 |
| 10,022,587 | B1* | 7/2018 | Wu | A61H 1/005 |
| 10,315,067 | B2* | 6/2019 | Tholkes | A61B 5/4566 |
| 10,894,182 | B2* | 1/2021 | Yoon | A63B 71/0054 |
| 2008/0234113 | A1* | 9/2008 | Einav | A61B 5/1116 |
| | | | | 482/66 |
| 2009/0318267 | A1* | 12/2009 | Park | A61H 3/00 |
| | | | | 482/8 |
| 2010/0298102 | A1* | 11/2010 | Bosecker | A61H 1/0237 |
| | | | | 482/54 |
| 2014/0100491 | A1* | 4/2014 | Hu | A63B 23/03541 |
| | | | | 601/27 |
| 2014/0371640 | A1* | 12/2014 | Schorgendorfer | A61H 1/0262 |
| | | | | 601/35 |
| 2015/0165265 | A1* | 6/2015 | Tholkes | A63B 23/03566 |
| | | | | 482/54 |
| 2016/0007885 | A1 | 1/2016 | Basta et al. | |
| 2016/0213972 | A1* | 7/2016 | Waldner | A61H 1/0262 |
| 2017/0007489 | A1* | 1/2017 | Lin | A61H 1/0262 |

* cited by examiner

GAIT TRAINING MACHINE AND METHOD OF USING SAME

BACKGROUND OF THE INVENTION

1. Field of the Invention

The present invention relates to gait training machinery, in particular to a gait training machine and its use method.

2. Description of the Related Art

With the rise of the health awareness of modern people, a variety of training equipment about physical function has also arisen. In terms of gait training, in addition to the treadmill with running function, it also began to focus on the training of healthy gait posture.

When an ordinary person walks, a gait cycle begins from the right heel to the ground to left toe off the ground, then, the left heel to the ground to the right toe off the ground and finally back to the right heel to the ground. It can be seen that the left and right feet will alternately change during the entire gait cycle, and the ankle joints of the left and right feet have different actuation angles at different times. Among them, during the maximum stride in the entire gait cycle, the ankle joint movement angle of the left and right feet is the largest.

Regarding the angle of action of the ankle joint, it is necessary to know that the angle of the ankle joint is different during the period of the asynchronous state. From the initial contact to the midstance, the ankle joint exhibits a dorsiflexion state. During the period from toe-off to mid-swing of the contralateral foot, the ankle join exhibits plantar flexion. This shows that the angle of the ankle joint is cyclic when the person is walking.

In addition, the body's center-of-gravity will also have a shift between the feet during the gait cycle. During the midstance, the center-of-gravity of the body will fall on the support foot and thus bear most of the weight of the body. By mid-swing, the center-of-gravity of the body is transferred to the opposite foot, and the weight of the body is absorbed by the opposite foot. It follows this cycle.

From the above, it is not difficult to understand that if you want to train healthy gait posture, you need to let the user know the movement of the ankle joint and the center-of-gravity between the feet to adjust the healthy gait posture.

At present, the related technical materials include the U.S. Pat. No. 7,266,424B2 patent, which incorporates one or more pressure sensors into the biped robot to capture state changes and information collection during the gait cycle, thereby controlling the joint drive unit to prevent falls and other actions.

The processor can perform calculations to obtain treadmill belt speed, foot impact time and left/right foot indication. The processor performs input data calculations from the sensor and obtains calculations related to gait parameters. In addition, the system provides recommendations for gait correction. For example, the system can instruct the user to change the direction of their feet, to rotate their ankles, to bend their knees more, or to correct or to modify the patient's gait based on other adjustments to the analysis of the patient's gait data.

SUMMARY OF THE INVENTION

The present invention has been accomplished under the circumstances in view. It is the main object of the present invention to provide a gait training machine and a method of using the same, which allows the user to know the movement of the ankle joint and the center-of-gravity of the body to adjust the healthy gait posture.

To achieve this and other objects of the present invention, a gait training machine comprising a base, a driving module, a sensor module, a controller and a signal processing module. The driving module is disposed in the base. The driving module comprises a driving circuit, a motor and two moving platforms. The driving circuit controls the motor to move the moving platforms. The sensor module comprises a left pedal, a right pedal, a plurality of pressure sensors and a position sensor. The left pedal and the right pedal are respectively pivotally connected to the moving platforms. The pressure sensors are respectively mounted on the left pedal and the right pedal. The position sensor is disposed in the base. The controller has the function of storing, processing and outputting data, and is electrically connected to the driving circuit, each pressure sensor and the position sensor. The signal processing module is disposed in the controller, comprising a gait detecting unit and a gait judgment unit. The gait judgment unit stores a center-of-gravity calculation logic and a gait determining logic. The motor drives the moving platforms to move the left pedal and the right pedal in the opposite direction. In the turning point of the reciprocating movement of each moving platform, the motor is reversely rotated, and at this time, the driving circuit generates a steering signal. When the left pedal and the right pedal pass the position sensor with the moving platforms, the position sensor generates a passing signal. The gait detecting unit receives weight signals detected by the pressure sensors, the passing signal detected by the position sensor and the steering signal provided by the driving circuit. The gait judgment unit receives the weight signals, the passing signal and the steering signal from the gait detecting unit, and uses the center-of-gravity calculation logic to calculate the bearing weight of the left pedal and the right pedal and the position of the center-of-gravity on the left pedal and right pedal, and also uses the gait determining logic to determine whether the bearing weight of the left pedal and the right pedal is correct and whether the position of the center-of-gravity is correct.

In this way, the user can know the movement of the ankle joint and the center-of-gravity of the body to adjust the health gait posture.

It is worth mentioning that the gait determining unit calculates the number of passes, the number of times of steering, the number of times that meet a first condition which indicates that the position of the center-of-gravity of said left pedal and said right pedal is correct, and the number of times that meet a second condition which indicates that the user's left foot and the right foot's ankle movement are correct. When the gait determining unit receives the passing signal, the number of passes is increased by one, and the gait determination logic is used to determine whether the bearing weight of the left pedal and the right pedal is correct. If correct, the number of times that meet said first condition is increased by one. If not, the number of times that meet said first condition is unchanged. When the gait judgment unit receives the steering signal, the number of times of steering is increased by one, and the gait determining logic is also used to determine whether the user's left foot and the right foot's ankle movement are correct. If correct, the number of times that meet said second condition is increased by one. If not, the number of times that meet said second condition remains unchanged.

Preferably, the gait training machine further comprises an evaluation module disposed at the controller. The evaluation module comprises a guiding unit. After the guiding unit receives the steering signal generated by the driving circuit, the guiding unit transmits a first guiding indicator to guide the user to move the center-of-gravity to one of the feet. After the guiding unit receives the steering signal again, the guiding unit transmits a second guiding indicator to guide the user to move the center-of-gravity to the other foot.

Preferably, the evaluation module further comprises a level-of-involvement evaluation unit that calculates an ankle joint correct rate and a center-of-gravity correct rate, the ankle joint correct rate=the number of times that meet said second condition/the number of times of steering*100%, the center-of-gravity correct rate=the number of times that meet said first condition/the number of passes*100%. This allows the user to evaluate the correct rate of gait posture.

To achieve this and other objects of the present invention, the invention provides a method of using a gait training machine. The gait training machine comprises a base, a driving module, a sensor module, a controller, a touch screen, a signal processing module and an evaluation module. The driving module comprises a driving circuit, a motor and two moving platforms. The sensor module comprises a left pedal, a right pedal, a plurality of pressure sensors and a position sensor. The left pedal and the right pedal are respectively pivotally connected to the moving platforms. The motor drives the moving platforms to move the left pedal and the right pedal in the opposite direction. The pressure sensors are respectively mounted on corners of the left pedal and the right pedal. The position sensor is disposed in the base. The touch screen is adapted for the user to input data and to display information. The controller is electrically connected to the driving circuit, each pressure sensor, the position sensor and the touch screen. The signal processing module is disposed in the controller, comprising a gait detecting unit and a gait determining unit. The gait determining unit stores a center-of-gravity calculation logic and a gait determining logic. The evaluation module is disposed in the controller, comprising a guiding unit. The method of using the gait training machine comprises the steps of:

A) preparation stage: where the user puts the both feet on the left pedal and the right pedal respectively, and the touch screen is for the user to set a speed level, a step distance, and a training time;

B) gait training machine action stage: where the controller converts the speed level, the step length and the training time into a driving data, and outputs the driving data to the driving circuit of the driving module for the driving circuit to control the rotation of the motor, thereby controlling the movement speed, the movement time and the range of motion of each of the moving platforms to drive the left pedal and the right pedal; the range of motion of each moving platform is limited to the step length; at the reciprocating turning point of each moving platform, the motor produces a reverse rotation, at this time, the driving circuit generates a steering signal; when the left pedal and the right pedal move with the respective moving platforms to pass the position sensor, the position sensor generates a passing signal;

C) signal detection and judgment: where the gait detecting unit receives a weight signal from each pressure sensor, the passing signal measured by the position sensor and the steering signal from the driving circuit, the gait judgment unit receives each weight signal from the gait detecting unit, the passing signal and the steering signal and uses the center-of-gravity calculation logic to calculate the bearing weight of the left pedal and the right pedal and the center-of-gravity position on the left pedal and the right pedal and also uses the gait determining logic to determine whether the bearing weight of the eft pedal and the right pedal is correct and whether the center-of-gravity position is correct; the gait judgment unit calculates the number of passes, the number of times of steering, the number of times that meet a first condition which indicates that the position of the center-of-gravity of said left pedal and said right pedal is correct and the number of times that meet a second condition which indicates that the user's left foot and the right foot's ankle movement are correct; when the gait judgment unit receives the passing signal, the number of passes is increased by one, and the gait determining logic is used to determine whether the bearing weight of the left pedal and the right pedal is correct, if correct, the number of times that meet said first condition is increased by one, and if not, the number of times that meet said first condition is unchanged; when the gait judgment unit receives the steering signal, the number of times of steering is increased by one, and the gait determining logic is used to determine whether the user's left foot and the right foot's ankle movement are correct, if all are correct, then the number of times that meet said second condition is increased by one, and if not, the number of times that meet said second condition is unchanged;

D) guiding display: after receiving the steering signal from the driving circuit in the process that the left pedal moves forward and the right pedal moves backward, the guiding unit transmits a left guiding signal to the touch screen, at this time, the touch screen displays a left arrow for guiding the user to move the center-of-gravity to the left foot, then, after receiving the steering signal again, the guiding unit transmits a right guiding signal to said touch screen, at this time, said touch screen displays a right arrow for guiding the user to move the center-of-gravity to the right foot; in addition, the guiding unit also receives from the gait judgment unit the result of determining whether the user's left and right ankle movements are correct, and the touch screen displays a left-shoe icon, a right-shoe icon, if the left ankle joint moves correctly, a left ankle joint display signal is sent to the touch screen, and the left-shoe icon is colored or illuminated after receiving the left ankle joint display signal for the user to understand that the left ankle joint moves correctly, if the right ankle joint moves correctly, a right ankle joint display signal is sent to the touch screen, and the right-shoe icon is colored or illuminated after receiving the right ankle joint display signal for the user to understand that the right ankle joint moves correctly; and E) repeated action: where steps B)-D) are repeated till said training time is ended.

In this way, the user can know and adjust the movement of the ankle joint and the center-of-gravity of the body to adjust the health gait posture.

It is worth mentioning that the valuation module further comprises a level-of-involvement evaluation unit, the method further comprises step F) after step E). In step F) result display: the level-of-involvement evaluation unit calculates an ankle joint correct rate and a center-of-gravity correct rate within the training time, the ankle joint correct rate=the number of times that meet said second condition/the number of times of steering*100%, the center-of-gravity correct rate=the number of times that meet said first condition/the number of passes*100%. The touch screen is able to be set to display the number of times that meet said second condition, the number of times of steering, the ankle joint correct rate, the number of times that meet said first condition, the number of passes, or the center-of-gravity correct rate.

It is worth mentioning that the determining logic is introduced as follows:

the gait judgment unit pre-stores a first threshold and a second threshold;

with respect to the center-of-gravity position of the user on the left pedal, the moving direction of the left pedal and the right pedal is the front-rear direction, and when the user stands on the left pedal and the right pedal, the side the user faces is the front side, Total LValue: left pedal bearing weight;
Total RValue: right pedal bearing weight;
Total Value: the user's weight;

Total Value=Total LValue+Total RValue;

when the left pedal moves backward and the passing signal is received, Total LValue/Total Value≥first threshold, it is determined that the user's body center-of-gravity is on the left foot, and the bearing weight of the left pedal is correct, if not, an error of the bearing weight of said left pedal is determined;

when the right pedal moves backward and the passing signal is received, Total RValue/Total Value≥first threshold, it is determined that the user's body center-of-gravity is on the right foot, and the bearing weight of the right pedal is correct, if not, an error of the bearing weight of the right pedal is determined;

define the forward moving direction of the left pedal and the right pedal as the X direction and the outward direction perpendicular to the X direction as the Y direction;

when |LX Position|/(LX_Proportion/2)≥ the second threshold, it indicates that the left ankle joint movement is correct, if not, it indicates that the left ankle joint movement is wrong;

LX_Position: the coordinate value of the center-of-gravity of the X direction on said left pedal;

LX_Proportion: the length of the left pedal along the X direction with the geometric center of the left pedal as the origin;

when |RX Position|/(RX_Proportion/2)≥ the second threshold, it indicates that the right ankle joint movement is correct, if not, it indicates that the right ankle joint movement is wrong;

RX Position: the coordinate value of the center-of-gravity of the X direction on the right pedal;

RX_Proportion: the length of the right pedal along the X direction with the geometric center of the right pedal as the origin.

In addition, it must be stated that the number of the pressure sensors is eight, which are respectively arranged in the four corners of the left pedal and the right pedal, and the pressure sensors on the left rear side, left front side, right front side and right rear side of the left pedal are defined as sensor A, sensor B, sensor C and sensor D respectively, and the pressure sensors on the right rear side, right front side, left front side and left rear side of the right pedal are defined as sensor E, sensor F, sensor G and sensor H respectively. When the user stands on the left pedal and the right pedal, the weight is applied to the left pedal and the right pedal;

Total LValue=LValue1+LValue2+LValue3+LValue4;

Total LValue: left pedal bearing weight;
LValue1: the weight signal detected by said sensor A;
LValue2: the weight signal detected by said sensor B;
LValue3: the weight signal detected by said sensor C;
LValue4: the weight signal detected by said sensor D;

Total RValue=RValue1+RValue2+RValue3+RValue4;

Total RValue: right pedal bearing weight;
RValue1: the weight signal detected by said sensor E;
RValue2: the weight signal detected by said sensor F;
RValue3: the weight signal detected by said sensor G;
RValue4: the weight signal detected by said sensor H;

Total Value=Total LValue+Total RValue;

Total Value: the user's weight.

then the center-of-gravity position on the left pedal is obtained by the following relationship:

$$LX\_Gravity=((LValue3+LValue2)*LX\_Proportion)/Total\ LValue;$$

$$LY\_Gravity=((LValue2+LValue1)*LY\_Proportion)/Total\ LValue;$$

LValue1: the weight signal detected by said sensor A;
LValue2: the weight signal detected by said sensor B;
LValue3: the weight signal detected by said sensor C;
LX_Proportion=the length of the left pedal along the X direction with the geometric center of the left pedal as the origin;
LY_Proportion=the length of the left pedal along the Y direction with the geometric center of the left pedal as the origin;

thus, the center-of-gravity coordinates on the left pedal (LX_Position, LY_Position) is obtained by the following relationship:

$$LX\_Position=LX\_Gravity-(LX\_Proportion/2);$$

$$LY\_Position=LY\_Gravity-(LY\_Proportion/2);$$

the center-of-gravity position on said right pedal is obtained by the following relationship:

$$RX\_Gravity=((RValue3+RValue2)*RX\_Proportion)/Total\ RValue;$$

$$RY\_Gravity=((RValue2+RValue1)*LY\_Proportion)/Total\ RValue;$$

RValue1: the weight signal detected by said sensor E;
RValue2: the weight signal detected by said sensor F;
RValue3: the weight signal detected by said sensor G;
RX_Proportion: the length of the right pedal along the X direction with the geometric center of the right pedal as the origin;
RY_Proportion: the length of the right pedal along the Y direction with the geometric center of the right pedal as the origin;

the center-of-gravity coordinates on the right pedal (RX_Position, RY_Position) is obtained by the following relationship:

$$RX\_Position=RX\_Gravity-(RX\_Proportion/2);$$

$$RY\_Position=RY\_Gravity-(RY\_Proportion/2).$$

It should be noted that the first threshold is 0.8 and the second threshold is 0.8.

To further guide the user's gait action, in the step D) guiding display, the left-shoe icon comprises a left-heel portion and a left-sole portion, and the right-shoe icon comprises a right-heel portion and a right-sole portion. When the guiding unit receives the steering signal during the process that the left pedal moves forward and the right pedal moves backward, the guiding unit transmits a first display signal to the touch screen, at this time, said left-heel portion is colored or illuminated to guide the user to put the center-of-gravity of the left foot on the left heel and also said right-sole portion is colored or illuminated to guide the user to put the center-of-gravity of the right foot on the right sole; then, the left pedal moves backward and the right pedal moves forward; when the guiding unit receives the passing signal, the guiding unit transmits a second display signal to the touch screen, at this time, the left-sole portion is colored or illuminated to guide the user to put the center-of-gravity of the left foot on the left sole and also the right-heel portion is colored or illuminated to guide the user to put the center-of-gravity of the right foot on the right heel.

Other advantages and features of the present invention will be fully understood by reference to the following specification in conjunction with the accompanying drawings, in which like reference signs denote like components of structure.

DETAILED DESCRIPTION OF THE INVENTION

Figure 1:
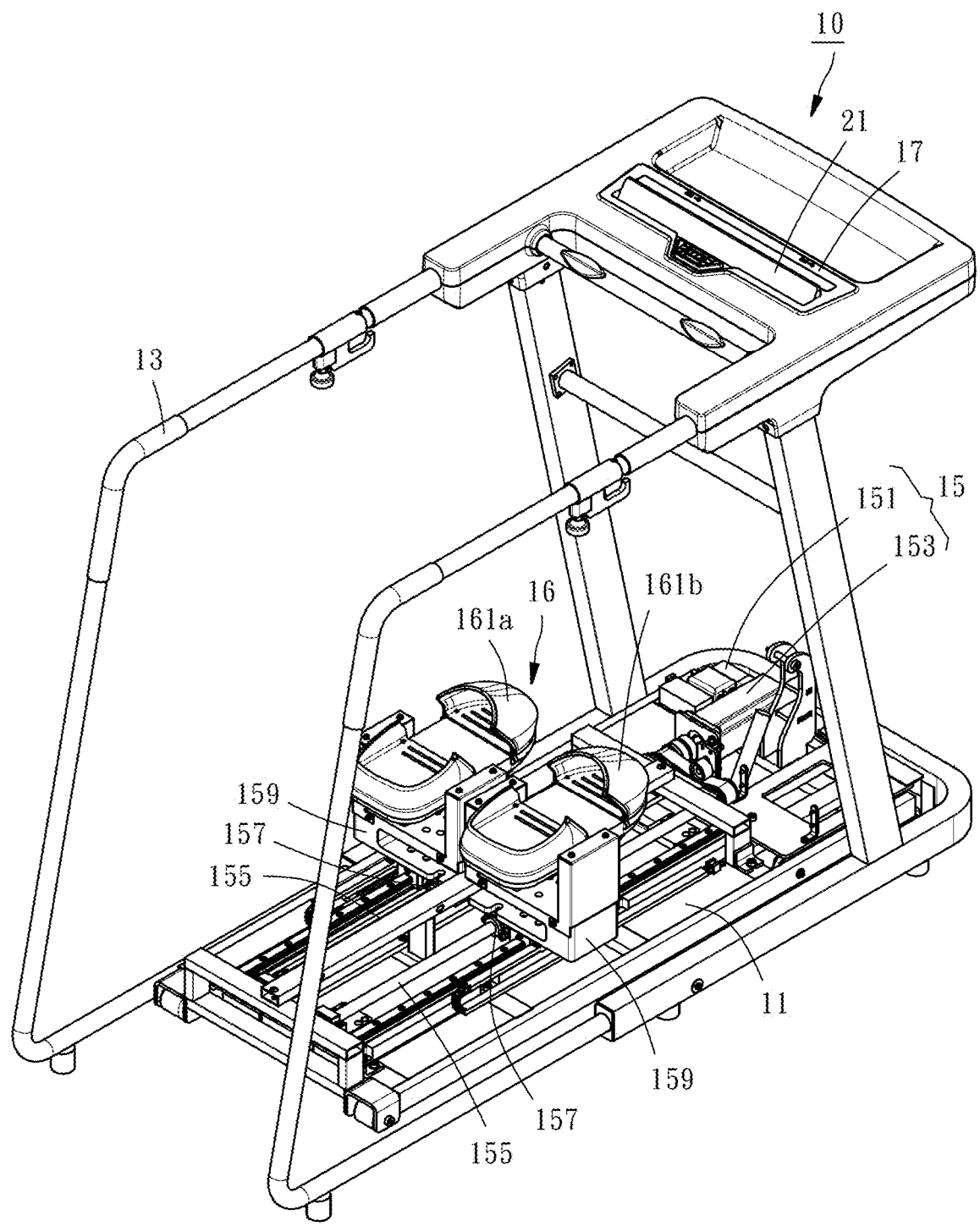
FIG. 1 is an oblique top elevational view of a gait training machine in accordance with the present invention.
Figure 2:
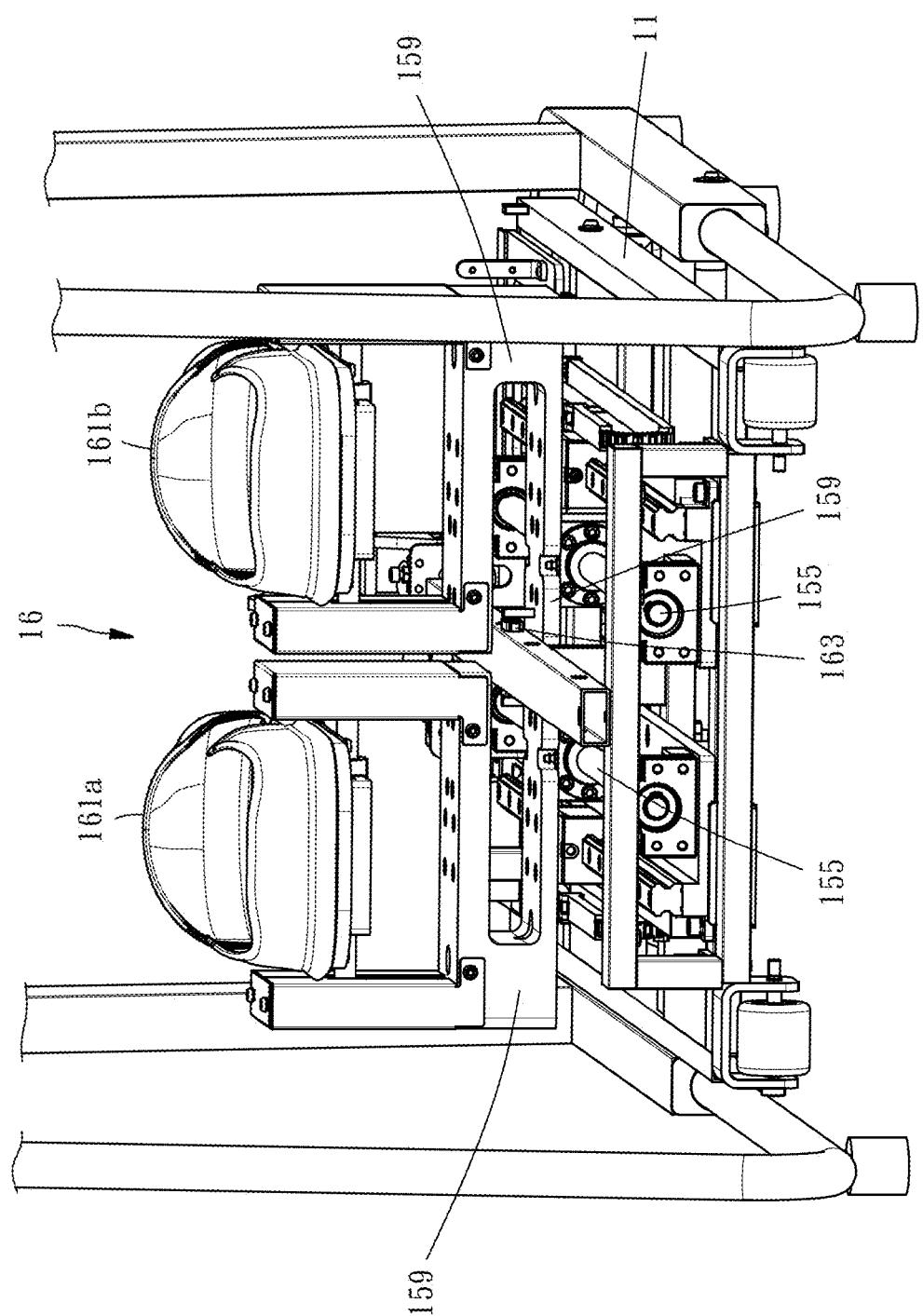
FIG. 2 is a rear elevation of a part of the gait training machine in accordance with the present invention.

Referring to FIGS. 1-5, the present invention provides a gait training machine 10. The gait training machine 10 includes a base 11, an armrest 13, a driving module 15, a sensing module 16, a controller 17, a signal processing module 171 and an evaluation module 172.

The base 11 is set on the ground.

The armrest 13 is mounted on the base 11 for the user to rest the arms when performing gait training. It should be noted that the armrest 13 is a component that assists the user and can be installed or removed.

The driving module 15 is disposed inside the base 11. The driving module 15 comprises a driving circuit 151 and a motor 153. The driving circuit 151 is used to control the motor 153. The motor 153 drives two screw rods 155. Two screw nuts 157 are respectively threaded onto the two screw rods 155. Two moving platforms 159 are respectively pivotally connected to the two screw nuts 157 and moved with the screw nuts 157 along the respective screw rods 155.

The sensor module 16 comprises a left pedal 161a, a right pedal 161b, a plurality of pressure sensors 162, and a position sensor 163.

The left pedal 161a and the right pedal 161b are respectively pivotally connected to the respective moving platforms 159. When the user's feet are respectively stepped on the left pedal 161a and the right pedal 161b, the moving platforms 159 move interactively to drive the user's gait movement, causing the left pedal 161a and the right pedal 161b to swing as the user's ankle joints rotate. The pressure sensors 162 are respectively disposed on the left pedal 161a and the right pedal 161b and used to measure the weight applied by the user's feet to generate a weight signal. It is worth mentioning that each pressure sensor 162 can be replaced by a load cell or a gyroscope.

The position sensor 163 is disposed in the base 11 on one side of the screw rods 155. When the moving platform 159 passes the position sensor 163, the position sensor 163 generates a passing signal. It is worth mentioning that in this embodiment, the position sensor 163 is a proximity switch, but any sensor capable of detecting the passage of an object can be used here, such as a photoelectric sensor, an electromagnetic sensor, or a capacitive sensor, etc.

The controller 17 has the function of storing, processing and outputting data.

The controller 17 is electrically connected to the driving circuit 151, each pressure sensor 162 and the position sensor 163.

The signal processing module 171 is disposed in the controller 17, comprising a gait detecting unit 171a and a gait judgment unit 171b. The gait judgment unit 171b stores a center-of-gravity calculation logic and a gait determining logic.

Wherein, the motor 153 drives the moving platforms 159 to move the left pedal 161a and the right pedal 161b in the opposite direction. In the turning point of the reciprocating movement of each moving platform 159, the motor 153 is reversely rotated. At this time, the driving circuit 151 generates a steering signal. When the left pedal 161a and the right pedal 161b pass the position sensor 163 with the moving platforms 159, the position sensor 163 generates a passing signal.

Wherein, the gait detecting unit 171a receives the weight signals detected by the pressure sensors 162, the passing signal detected by the position sensor 163 and the steering signal provided by the driving circuit 151. The gait judgment unit 171b receives the weight signals, the passing signal and the steering signal from the gait detecting unit 171a, and uses the center-of-gravity calculation logic to calculate the bearing weight of the left pedal 161a and the right pedal 161b and the position of the center-of-gravity on the left pedal 161a and the right pedal 161b, and also uses the gait determining logic to determine whether the bearing weight of the left pedal 161a and the right pedal 161b is correct and whether the position of the center-of-gravity is correct.

With the above-mentioned gait training machine, the user can know the movement of the ankle joint and the center-of-gravity of the body to adjust the healthy gait posture.

It is worth mentioning that the gait judgment unit 171b can calculate the number of passes, the number of times of steering, the number of times that meet a first condition which indicates that the position of the center-of-gravity of said left pedal and said right pedal is correct, and the number of times that meet a second condition which indicates that the user's left foot and the right foot's ankle movement are correct. When the gait judgment unit 171b receives the passing signal, the number of passes is increased by one. The gait determination logic is used to determine whether the bearing weight of the left pedal 161a and the right pedal 161b is correct. If correct, the number of times that meet said first condition is increased by one. If not, the number of times that meet said first condition is unchanged. When the gait judgment unit 171b receives the steering signal, the number of times of steering is increased by one. Further, the gait determining logic is also used to determine whether the user's left foot and the right foot's ankle movement are correct. If correct, the number of times that meet said second condition is increased by one. If not, the number of times that meet said second condition remains unchanged.

In addition, this embodiment also selects to include an evaluation module 172. The evaluation module 172 is disposed at the controller 17, comprising a guiding unit 172a. After the guiding unit 172a receives the steering signal generated by the driving circuit 151, the guiding unit 172a transmits a first guiding indicator to guide the user to move the center-of-gravity to one of the feet. After the guiding unit 172a receives the steering signal again, the guiding unit 172a transmits a second guiding indicator to guide the user to move the center-of-gravity to the other foot.

In this embodiment, the evaluation module 172 further comprises a level-of-involvement evaluation unit 172b that calculates an ankle joint correct rate and a center-of-gravity correct rate. The ankle joint correct rate=the number of times that meet said second condition/the number of times of steering*100%. The center-of-gravity correct rate=the number of times that meet said first condition/the number of passes*100%. It also allows the user to know the movement of the ankle joint and the movement of the center-of-gravity of the body.

The above is the introduction of the gait training machine 10 provided by the present invention. Next, as shown in FIGS. 6-13, the second embodiment of the present invention provides a method for using the gait training machine 10.

It should be noted that, in this embodiment, the gait training machine provided by the first embodiment of the present invention is used, and the controller 17 is electrically connected to a touch screen 21. As shown in FIG. 1, the touch screen 21 is used for inputting data by the user and displaying information.

Figure 3:
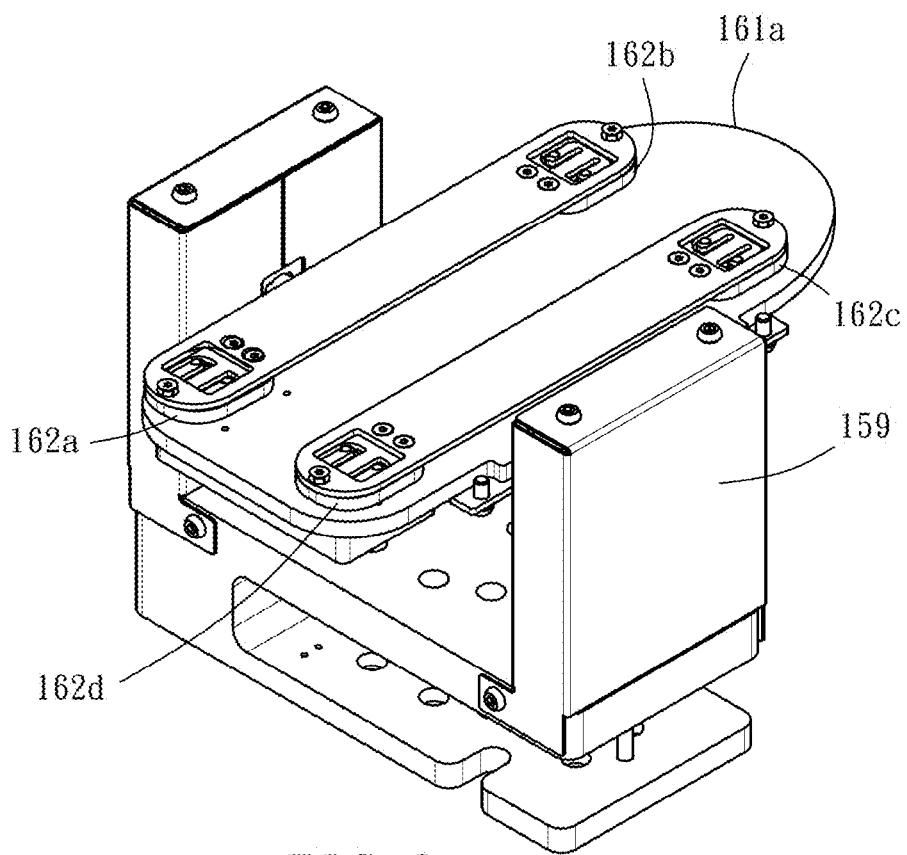
FIG. 3 is a partial elevational view of the gait training machine in accordance with the present invention, illustrating the structure of the left pedal.
Figure 4:
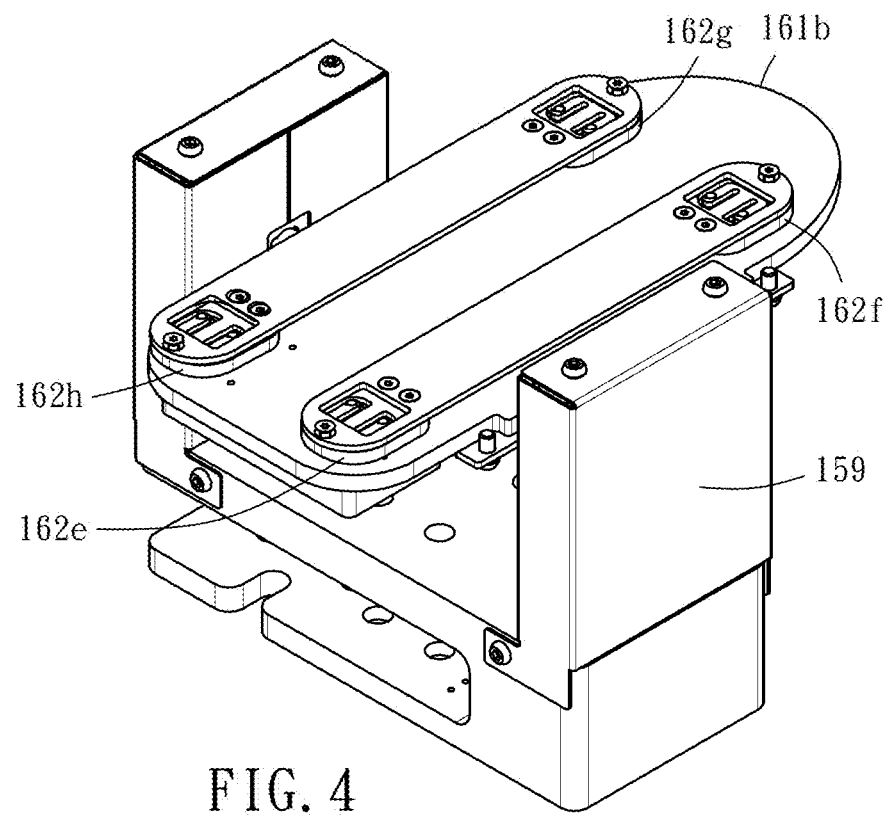
FIG. 4 is a partial elevational view of the gait training machine in accordance with the present invention, illustrating the structure of the right pedal.
Figure 5:
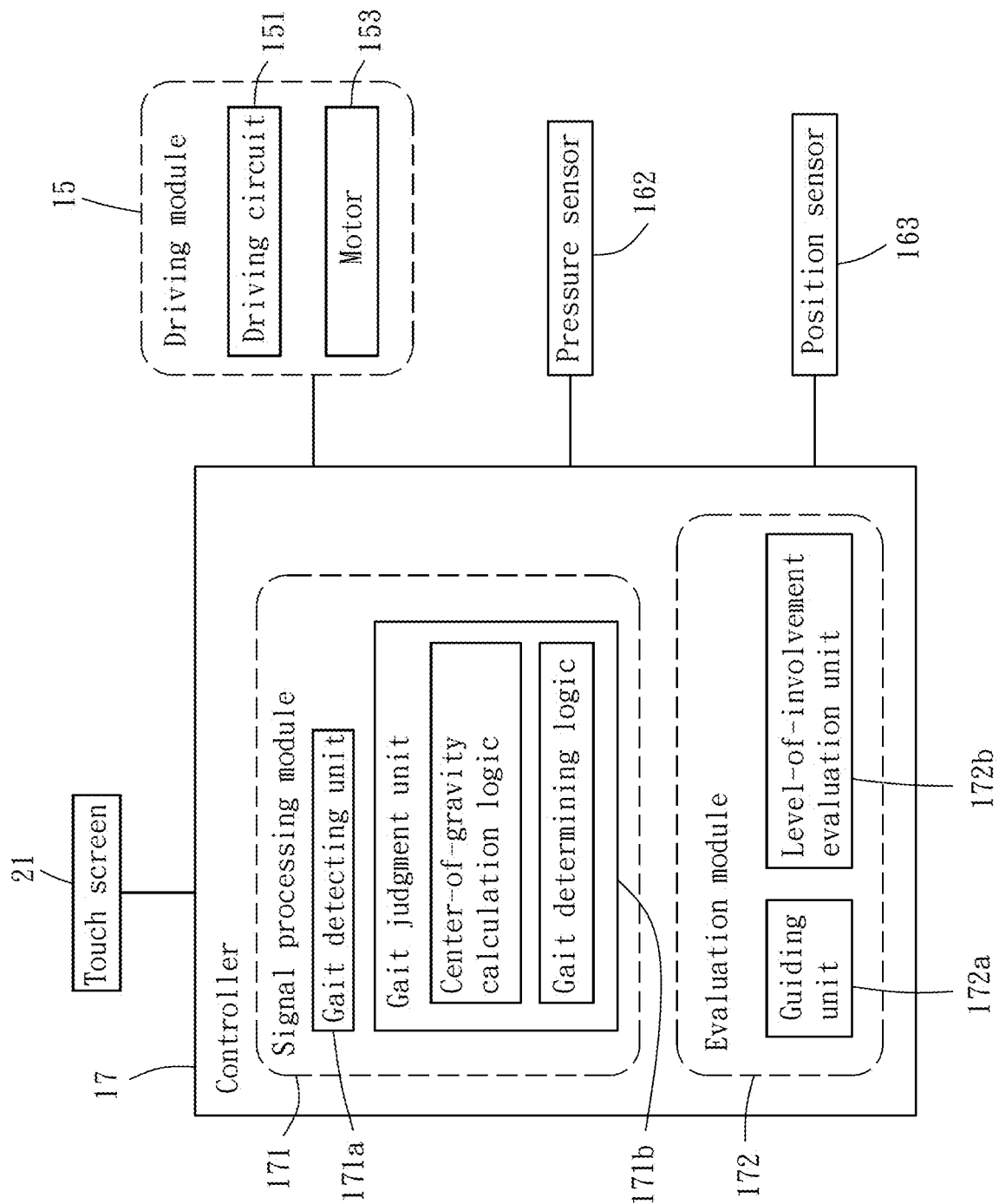
FIG. 5 is a system block diagram of the gait training machine in accordance with the present invention, illustrating the arrangement of the controller, the driving module, the pressure sensor and the position sensor.
Figure 6:
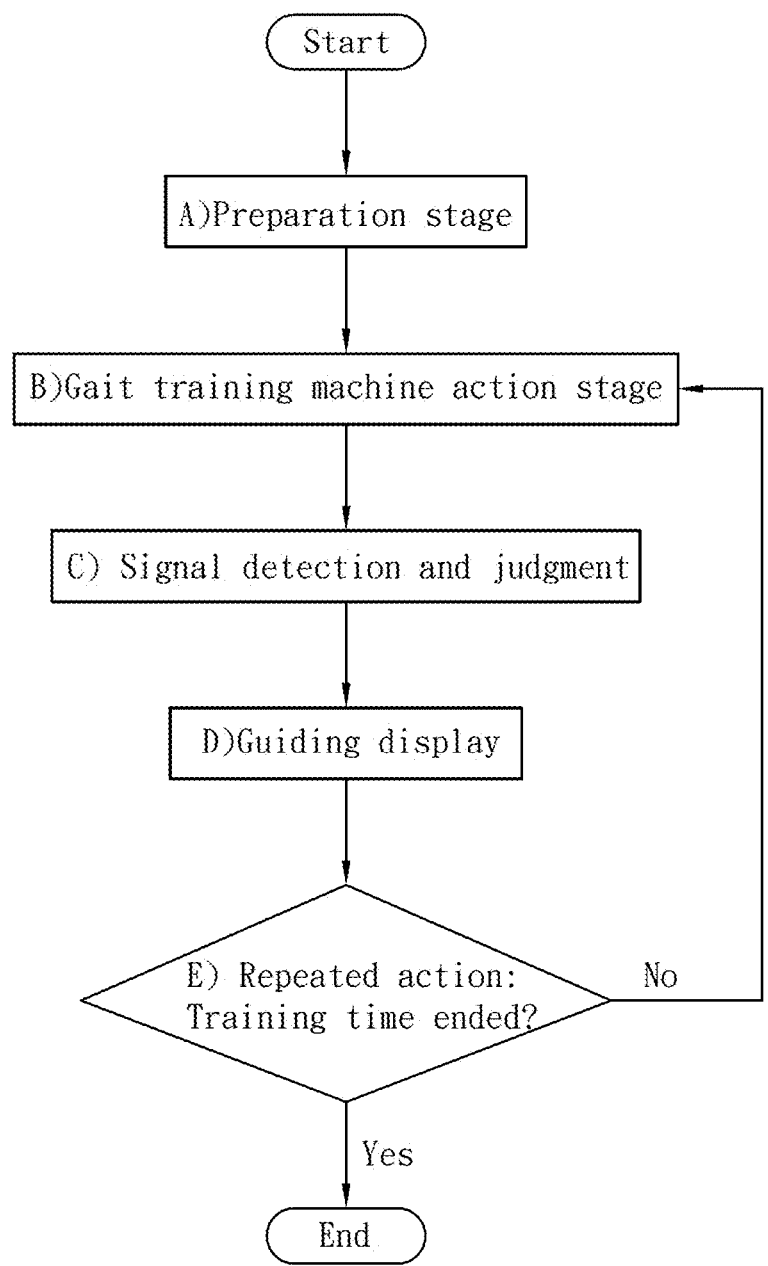
FIG. 6 is a flow chart of a gait training machine using method in accordance with the present invention, showing steps A)-E).

In addition, in the present embodiment, as shown in FIGS. 3 and 4, the number of the pressure sensors 162 is eight, which are respectively disposed at the four corners of the left pedal 161a and the right pedal 161b. The pressure sensors 162 on the left rear side, left front side, right front side and right rear side of the left pedal 161a are sensor A (162a), sensor B (162b), sensor C (162c) and sensor D (162d) respectively. The pressure sensors 162 on the right rear side, right front side, left front side and left rear side of the right pedal 161b are sensor E (162e), sensor F (1621), sensor G (162g), sensor H (162h) respectively.

The method of using the gait training machine 10 includes the following steps:

A) Preparation stage: The user puts the both feet on the left pedal 161a and the right pedal 161b respectively. The touch screen 21 is for the user to set a speed level, a step distance, and a training time.

The controller 17 displays a plurality of speed levels on the touch screen 21 for the user to select one of the speed levels.

Each speed level indicates the moving speed of the moving platform 159, from fast to slow or from slow to fast. For example, the moving platform 159's moving speed is divided into 4 levels. As a result of slow to fast, the moving speed of the moving platform 159 at the fourth level is faster than the third level faster than the second level faster than the second level. It should be noted that when the moving platform 159 reciprocates, its speed distribution can be divided into an acceleration section, a constant speed section and a deceleration section. Here, the speed level refers to the moving speed grading of the moving platform at the constant speed section.

The controller 17 also displays a step length field on the touch screen 21 for the user to input a step length. The step length in the gait training machine 10 reflects the distance of the corresponding position on the left pedal 161a and the right pedal 161b, for example, the distance between the rear end point of the left pedal 161a and the rear end point of the right pedal 161b is 80 cm, that is, input 80 cm.

The controller 17 also displays a gait training time field on the touch screen 21 for the user to input a training time data, for example, 30 minutes, 40 minutes.

B) Gait Training Machine Action Stage:

The controller 17 converts the speed level, the step length and the training time into a driving data, and outputs the driving data to the driving circuit 151 of the driving module 15, for the driving circuit 151 to control the rotation of the motor 153, thereby controlling the movement speed, the movement time and the range of motion of each of the moving platforms 159 to drive the left pedal 161a and the right pedal 161b. The range of motion of each moving platform 159 is limited to the step length. At the reciprocating turning point of each moving platform 159, the motor 153 produces a reverse rotation. At this time, the driving circuit 151 generates a steering signal. When the left pedal 161a and the right pedal 161b move with the respective moving platforms 159 to pass the position sensor 163, the position sensor 163 generates a passing signal.

Here, after the left pedal 161a or the right pedal 161b is located at the turning point in the moving direction, the next moving direction will be switched, for example, the left pedal 161a (or the right pedal 161b) moves forward to the end of the stroke, and then moves backward; the left pedal 161a (or the right pedal 161b) moves backward to the end of the stroke, and then moves forward.

C) Signal Detection and Judgment:

The gait detecting unit 171a receives a weight signal from each pressure sensor 162, the passing signal measured by the position sensor 163 and the steering signal from the driving circuit 151. The gait judgment unit 171b receives each weight signal from the gait detecting unit 171a, the passing signal and the steering signal, and uses the center-of-gravity calculation logic to calculate the bearing weight of the left pedal 161a and the right pedal 161b and the center-of-gravity position on the left pedal 161a and the right pedal 161b, and also uses the gait determining logic to determine whether the bearing weight of the left pedal 161a and the right pedal 161b is correct and whether the center-of-gravity position is correct. The gait judgment unit 171b calculates the number of passes, the number of times of steering, the number of times that meet a first condition which indicates that the position of the center-of-gravity of said left pedal and said right pedal is correct, the number of times that meet a second condition which indicates that the user's left foot and the right foot's ankle movement are correct. When the gait judgment unit 171b receives the passing signal, the number of passes is increased by one, and the gait determining logic is used to determine whether the bearing weight of the left pedal 161a and the right pedal 161b is correct. If correct, the number of times that meet said first condition is increased by one, and if not, the number of times that meet said first condition is unchanged. When the gait judgment unit 171b receives the steering signal, the number of times of steering is increased by one, and the gait determining logic is used to determine whether the user's left foot and the right foot's ankle movement are correct. If all are correct, then the number of times that meet said second condition is increased by one, and if not, the number of times that meet said second condition is unchanged.

The center-of-gravity calculation logic is described below.

When the user stands on the pedals, the weight is applied to the left pedal 161a and the right pedal 161b.

$$\text{Total } L\text{Value} = L\text{Value1} + L\text{Value2} + L\text{Value3} + L\text{Value4};$$

Total LValue: left pedal bearing weight;
LValue1-4: weight signals of sensors A-D;

$$\text{Total } R\text{Value} = R\text{Value1} + R\text{Value2} + R\text{Value3} + R\text{Value4};$$

Total RValue: right pedal bearing weight;
RValue1-4: the weight signals of sensors E-H;
Total Value=Total LValue+Total RValue;
Total Value: the user's weight.

Then, calculate the center-of-gravity position.

With respect to the center-of-gravity position of the user on the left pedal 161a, the moving direction of the left pedal 161a and the right pedal 161b is the front-rear direction. When the user stands on the left pedal 161a and the right pedal 161b, the front side faces the X direction. The outward direction perpendicular to the X direction is the Y direction. Under this circumstance, the center-of-gravity position is calculated by the following relationship:

$$LX\_\text{Gravity} = ((L\text{Value3} + L\text{Value2})*LX\_\text{Proportion})/\text{Total } L\text{Value};$$

$$LY\_\text{Gravity} = ((L\text{Value2} + L\text{Value1})*LY\_\text{Proportion})/\text{Total } L\text{Value};$$

LValue1-3: Weight signals of sensors A-C;
LX_Proportion=the length of the left pedal along the X direction with the geometric center of the left pedal 161a as the origin;
LY_Proportion=the length of the left pedal along the Y direction with the geometric center of the left pedal 161a as the origin;

Thus, the center-of-gravity coordinates is on the left pedal 161a:

$$LX\_\text{Position} = LX\_\text{Gravity} - (LX\_\text{Proportion}/2);$$

$$LY\_\text{Position} = LY\_\text{Gravity} - (LY\_\text{Proportion}/2);$$

(LX_Position, LY_Position)=Center-of-gravity coordinates on the left pedal 161a.

The center-of-gravity position on the right pedal 161b:

$$RX\_\text{Gravity} = ((R\text{Value3} + R\text{Value2})*RX\_\text{Proportion})/\text{Total } R\text{Value};$$

$$RY\_\text{Gravity} = ((R\text{Value2} + R\text{Value1})*LY\_\text{Proportion})/\text{Total } R\text{Value};$$

RValue1-3: Weight signals of sensors E-G
RX_Proportion=the length of the right pedal along the X direction with the geometric center of the right pedal 161b as the origin;
RY_Proportion=the length of the right pedal along the Y direction with the geometric center of the right pedal 161b as the origin.

Thus, the center-of-gravity coordinates on the right pedal 161b:

$$RX\_\text{Position} = RX\_\text{Gravity} - (RX\_\text{Proportion}/2);$$

$$RY\_\text{Position} = RY\_\text{Gravity} - (RY\_\text{Proportion}/2);$$

(RX_Position, RY_Position)=the center-of-gravity coordinates on the right pedal 161b.

Figure 7:
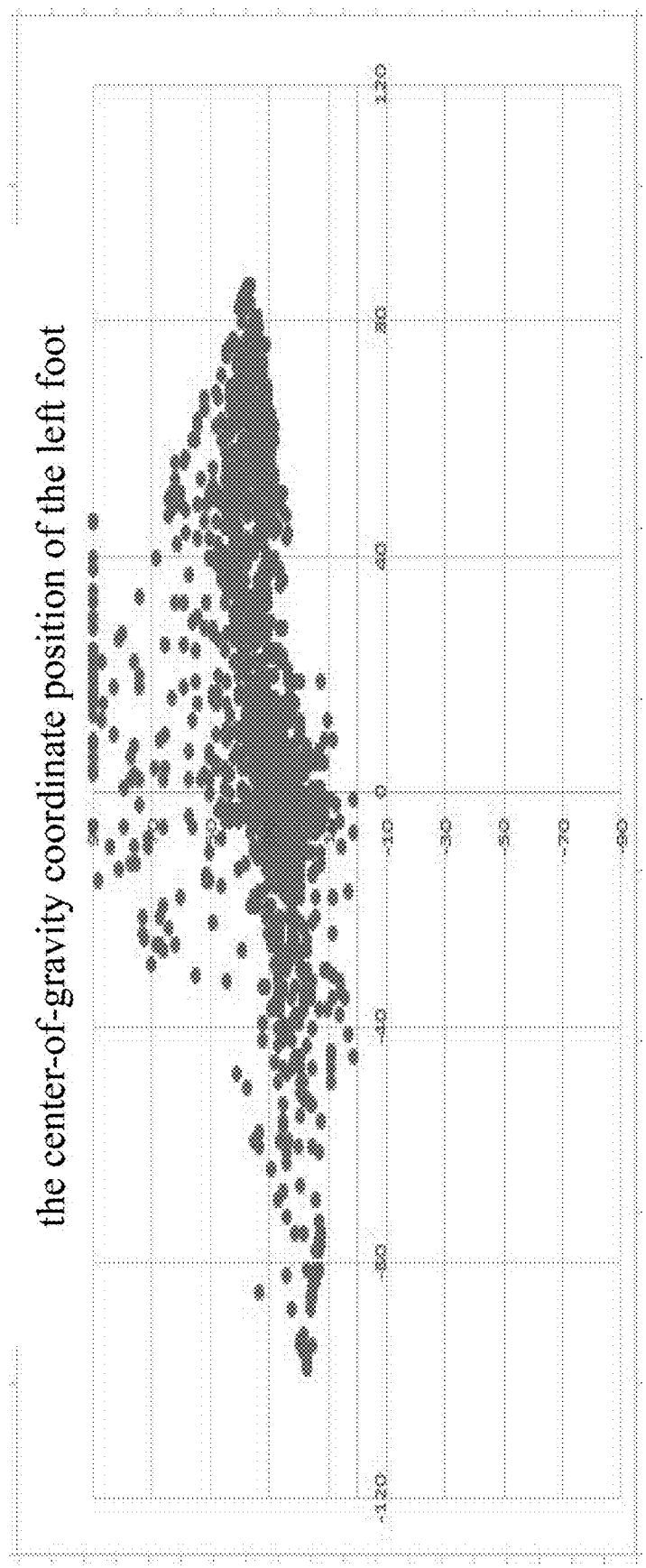
FIG. 7 is a schematic drawing of the gait training machine using method in accordance with the present invention, showing the distribution of the center-of-gravity coordinate position of the left pedal.
Figure 8:
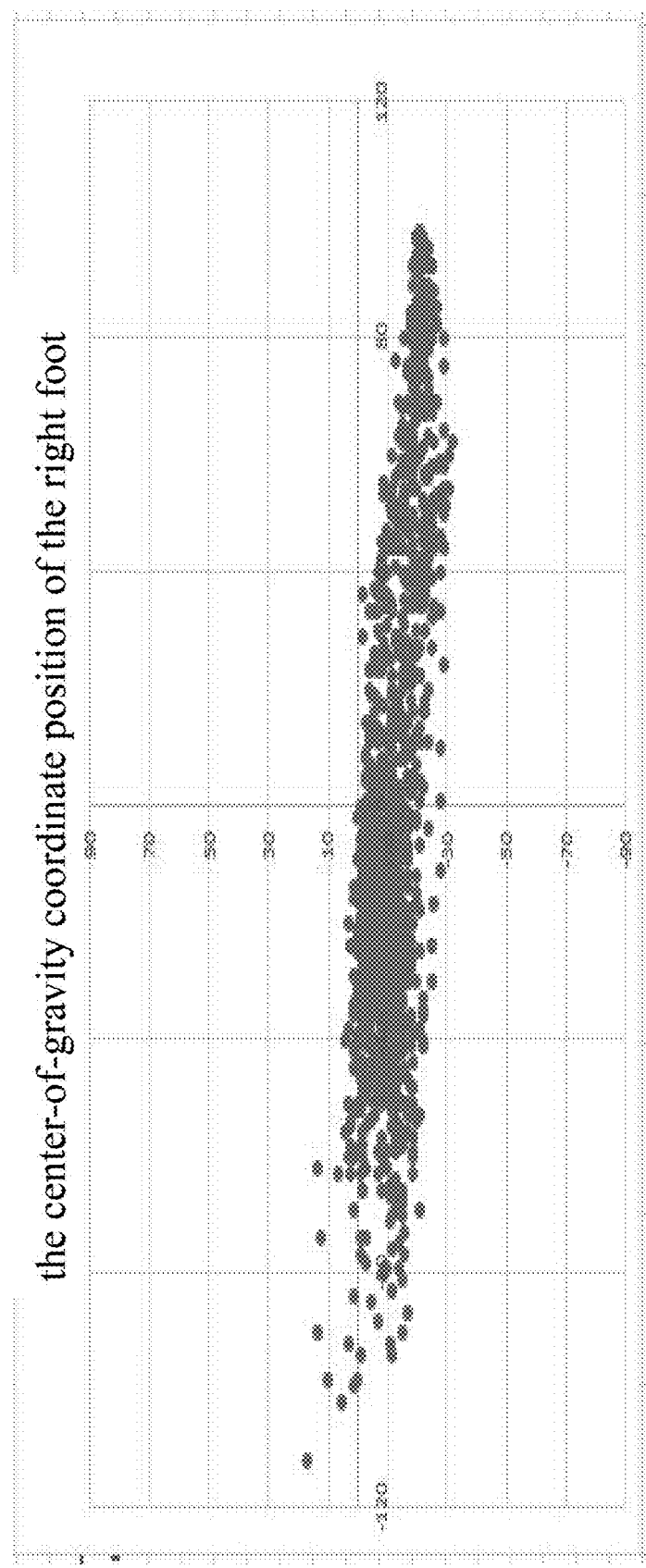
FIG. 8 is a schematic drawing of the gait training machine using method in accordance with the present invention, showing the distribution of the center-of-gravity coordinate position of the right pedal.

As shown in FIG. 7, the gravity center coordinate position distribution diagram on the left pedal 161a is exemplified, the X direction coordinate indicates the length of the left pedal 161a, and the Y coordinate indicates the width of the left pedal 161a. As shown in FIG. 8, the gravity center coordinate position distribution diagram on the right pedal 161b is exemplified, the X direction coordinate indicates the length of the right pedal 161b, and the Y coordinate indicates the width of the left pedal 161a. The value of each point in FIGS. 7 and 8 is the center-of-gravity position of the left pedal 161a or right pedal 161b in the training time calculated by the center-of-gravity calculation logic by a preset sampling frequency. For example, when the sampling frequency is 0.2 (Hz), it means that the pressure sensors 162 on the left pedal 161a and the right pedal 161b measure the weight signal once per every 5 seconds. The sampling frequency can also be set to other values, not limited to this.

The gait determining logic is introduced as follows:

The gait judgment unit 171b pre-stores a first threshold and a second threshold.

When the left pedal 161a moves backward and the passing signal is received, Total LValue/Total Value≥first threshold, it is determined that the user's body center-of-gravity is on the left foot, and the bearing weight of the left pedal 161a is correct; if not, an error of the bearing weight of the left pedal 161a is determined.

When the right pedal 161a moves backward and the passing signal is received, Total RValue/Total Value≥first threshold, it is determined that the user's body center-of-gravity is on the right foot, and the bearing weight of the right pedal 161a is correct; if not, an error of the bearing weight of the right pedal 161a is determined.

It is worth mentioning that in the present embodiment, the first threshold is 0.8, but a value of 0.5 or more may be selected according to requirements; if the first threshold is lower than 0.5, the center-of-gravity of the body is on the other side, and there is no benefit of determining the center-of-gravity of the body; if the first threshold is higher than 1, the unilateral body weight is higher than the whole body weight, which is a wrong situation.

In addition, the gait judgment unit 171b also pre-stores the second threshold.

|LX_Position|/(LX_Proportion/2)≥said second threshold, it indicates that the left ankle joint is moving correctly; if not, it indicates that the left ankle joint movement is wrong;

|RX_Position|/(RX_Proportion/2)≥said second threshold, it indicates that the right ankle joint is moving correctly; if not, it indicates that the right ankle joint movement is wrong.

In this embodiment, the second threshold is 0.8, but a value of 0.5 or more may also be selected according to requirements. Since |LX_Position| represents the distance of the center-of-gravity position on the left pedal 161a from the origin of the left pedal 161a in the X direction, |RX_Position| represents the distance of the center-of-gravity position on the right pedal 161b from the origin of the right pedal 161b in the X direction, so the greater the value of |LX_Position| and |RX_Position|, the greater the angle of ankle joint movement and the greater the degree of ankle joint movement. Therefore, if the second threshold is lower than 0.5, the movement angle of the ankle joint is insufficient, and there is no training benefit; if the second threshold is higher than 1, the center-of-gravity coordinates is outside the left and the right pedal, which is a wrong situation.

Figure 9:
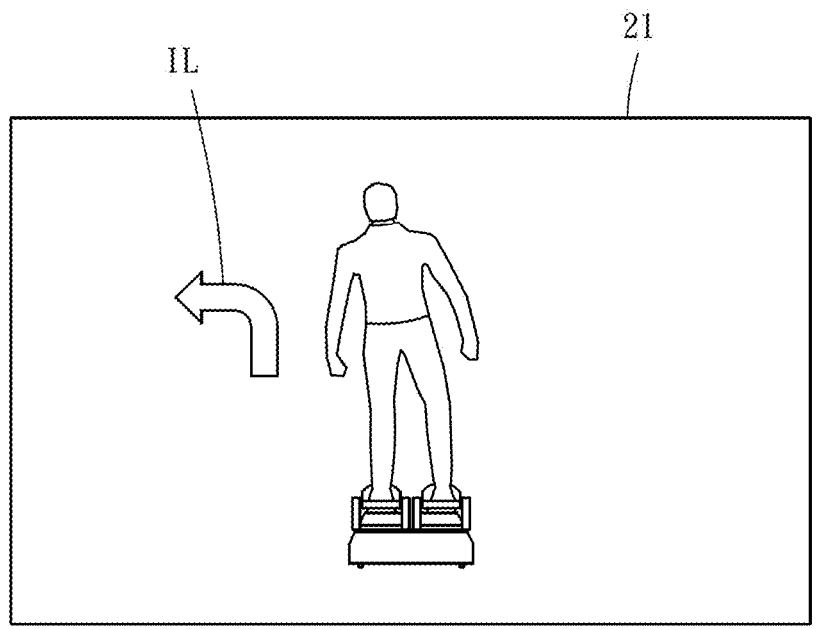
FIG. 9 is a schematic drawing of the gait training machine using method in accordance with the present invention, showing a left arrow displayed on the touch screen to guide the user to move the center-of-gravity of the body to the left foot.
Figure 10:
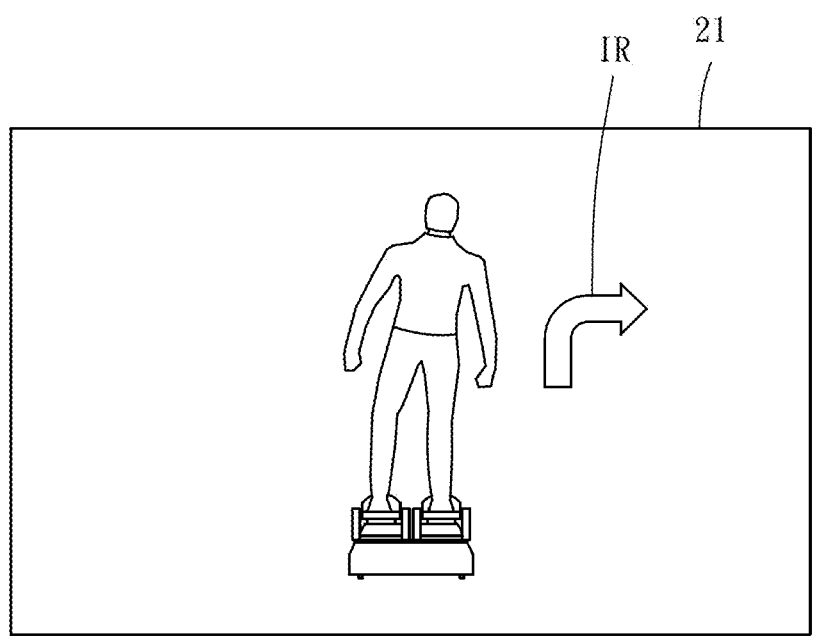
FIG. 10 is a schematic drawing of the gait training machine using method in accordance with the present invention, showing a right arrow displayed on the touch screen to guide the user to move the center-of-gravity of the body to the right foot.

D) Guiding Display:

As shown in FIGS. 9 and 10, after receiving the steering signal from the driving circuit 151 in the process that the left pedal 161a moves forward and the right pedal 161b moves backward, the guiding unit 172a transmits a left guiding signal to the touch screen 21. At this time, the touch screen 21 displays a left arrow IL for guiding the user to move the center-of-gravity to the left foot. Then, after receiving the steering signal again, the guiding unit 172a transmits a right guiding signal to the touch screen 21. At this time, the touch screen 21 displays a right arrow IR for guiding the user to move the center-of-gravity to the right foot. Such displays are cycled to guide the user to change the position of the center-of-gravity in the gait.

After receiving the steering signal from the driving circuit 151 in the process that the left pedal 161a moves backward and the right pedal 161b moves forward, the guiding unit 172a transmits the right guiding signal to the touch screen 21. At this time, the touch screen 21 displays the right arrow IR for guiding the user to move the center-of-gravity to the right foot. Then, after receiving the steering signal again, the guiding unit 172a transmits the left guiding signal to the touch screen 21. At this time, the touch screen 21 displays the left arrow IL for guiding the user to move the center-of-gravity to the left foot. Such displays are cycled to guide the user to change the position of the center-of-gravity in the gait.

Figure 11:
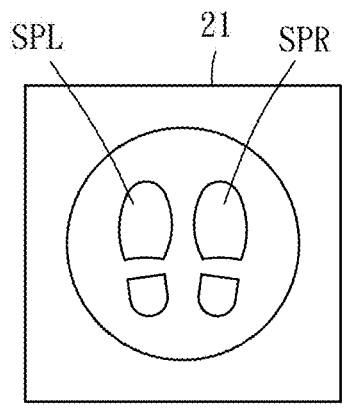
FIG. 11 is a schematic drawing of the gait training machine using method in accordance with the present invention, showing a left-shoe icon and a right-shoe icon displayed on the touch screen.

In addition, as shown in FIG. 11, the guiding unit 172a also receives a result from the gait judgment unit 171b to determine whether the ankle joint movement of the left and right feet of the user is correct.

In addition, as shown in FIG. 11, the guiding unit 172a also receives from the gait judgment unit 171b the result of determining whether the user's left and right ankle movements are correct. The touch screen 21 displays a left-shoe icon SPL, a right-shoe icon SPR. If the left ankle joint moves correctly, a left ankle joint display signal is sent to the touch screen 21, and the left-shoe icon SPL is colored or illuminated after receiving the left ankle joint display signal for the user to understand that the left ankle joint moves correctly. If the right ankle joint moves correctly, a right ankle joint display signal is sent to the touch screen 21, and the right-shoe icon SPR is colored or illuminated after receiving the right ankle joint display signal for the user to understand that the right ankle joint moves correctly. The display cycle is repeated for the user to understand the correct movement of the left and right ankle joints.

Figure 12:
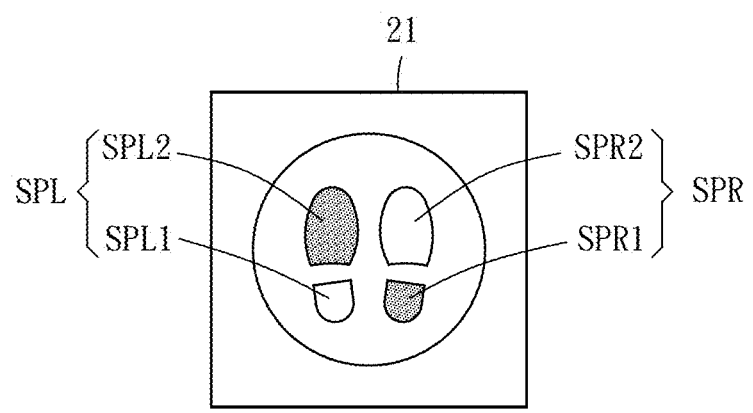
FIG. 12 is a schematic drawing of the gait training machine using method in accordance with the present invention, showing a left-heel portion, a left-sole portion, a right-heel portion and a right-sole portion displayed on the touch screen.

It is worth mentioning that, as shown in FIG. 12, the left-shoe icon SPL displayed by the touch screen 21 can be further divided into a left-heel portion SPL1 and a left-sole portion SPL2, and the right-shoe icon SPR is further divided into right-heel portion SPR1 and right-sole portion SPR2.

After receiving the steering signal from the driving circuit 151 in the process that the left pedal 161a moves forward and the right pedal 161b moves backward, the guiding unit 172a simultaneously transmits a first display signal to the touch screen 21. After receiving the left heel display signal, the touch screen 21 colors or illuminates the left-heel portion SPL1 to indicate the user to put the center-of-gravity of the left foot on the left heel. After receiving the right sole display signal, the touch screen 21 colors or illuminates the right-sole portion SPR2 to indicate the user to put the center-of-gravity of the right foot on the right sole. Then, after receiving the passing signal of the position sensor 163, a second display signal are simultaneously sent to the touch screen 21.

After receiving the left sole display signal, the touch screen 21 colors or illuminates the left-sole portion SPL2 to indicate the user to put the center-of-gravity of the left foot on the left sole. After receiving the right heel display signal, the touch screen 21 colors or illuminates the right-heel portion SPR1 to indicate the user to put the center-of-gravity of the right foot on the right heel.

E) Repeated Action:

Repeat steps B)-D) until the training time is up.

Figure 13:
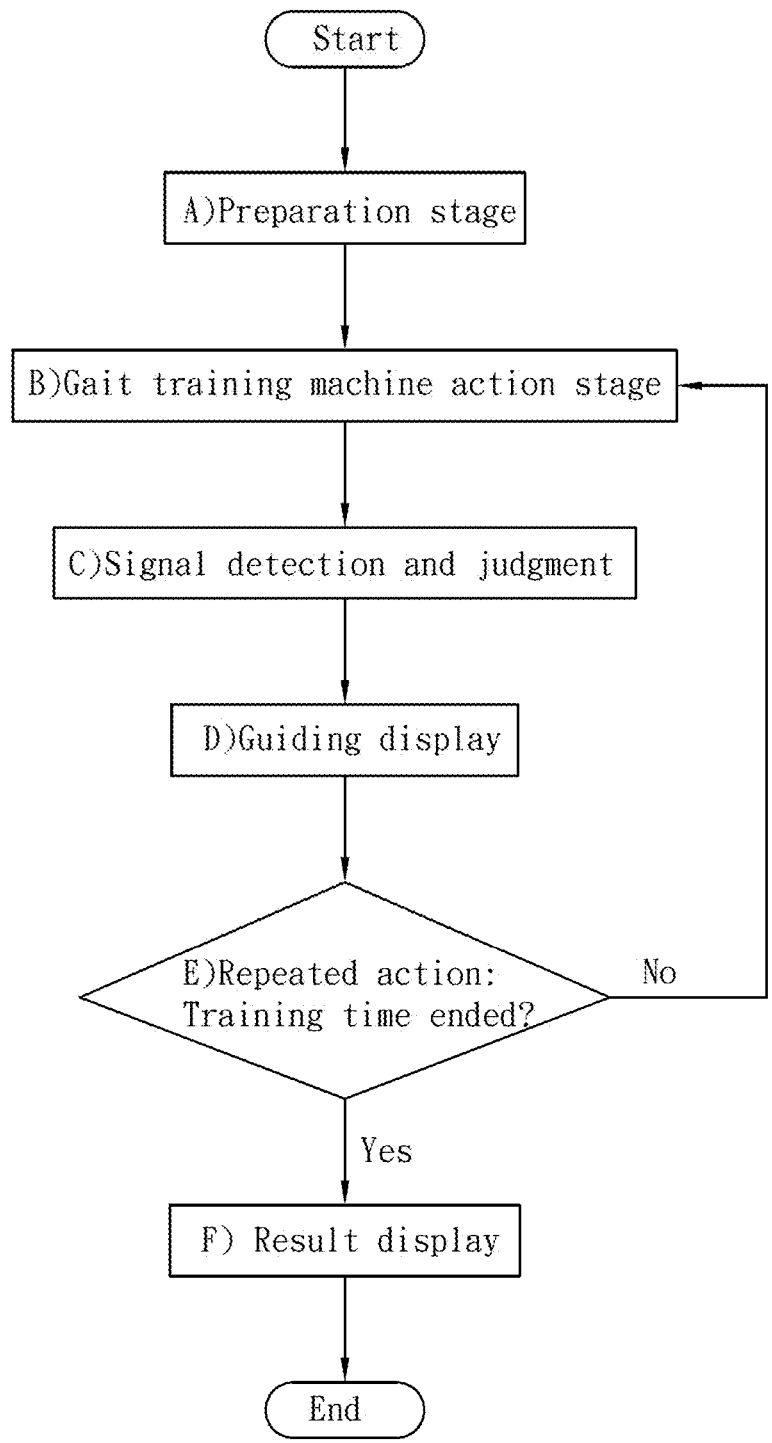
FIG. 13 is a flow chart of a gait training machine using method in accordance with the present invention, showing steps A)-F).

It is worth mentioning that, as shown in FIG. 13, step F) may be added after step E).

F) Result Display:

The level-of-involvement evaluation unit 172b calculates an ankle joint correct rate and a center-of-gravity correct rate within the training time, wherein the ankle joint correct rate=the number of times that meet said second condition/the number of times of steering*100%; the center-of-gravity correct rate=the number of times that meet said first condition/the number of passes*100%; the touch screen 21 can be set to display the number of times that meet said second condition, the number of times of steering, the ankle joint correct rate, the number of times that meet said first condition, the number of passes, or the center-of-gravity correct rate.

In this way, during the gait training, the user is informed of the ankle movement and the center-of-gravity of the body to adjust the healthy gait posture.

What is claimed is:

1. A gait training machine, comprising:
   a base;
   a driving module disposed in said base, said driving module comprising a driving circuit, a motor and two moving platforms, said driving circuit controlling said motor to move said moving platforms;
   a sensor module comprising a left pedal, a right pedal, a plurality of pressure sensors and a position sensor, said left pedal and said right pedal being respectively pivotally connected to said moving platforms, said pressure sensors being respectively mounted on said left pedal and said right pedal, said position sensor being disposed in said base;

a controller having the function of storing, processing and outputting data, said controller being electrically connected to said driving circuit, each said pressure sensor and said position sensor;

a signal processing module disposed in said controller, said signal processing module comprising a gait detecting unit and a gait judgment unit, said gait judgment unit storing a center-of-gravity calculation logic and a gait determining logic;

wherein, said motor drives said moving platforms to move said left pedal and said right pedal in the opposite direction; in the turning point of the reciprocating movement of each said moving platform, said motor is reversely rotated, and at this time, said driving circuit generates a steering signal; when said left pedal and said right pedal pass said position sensor, said position sensor generates a passing signal;

wherein, said gait detecting unit receives weight signals detected by said pressure sensors, said passing signal detected by said position sensor and said steering signal provided by said driving circuit; said gait judgment unit receives said weight signals, said passing signal and said steering signal from said gait detecting unit, and uses said center-of-gravity calculation logic to calculate the bearing weight of said left pedal and said right pedal and the position of the center-of-gravity on said left pedal and said right pedal, and also uses said gait determining logic to determine whether the bearing weight of said left pedal and said right pedal is correct and whether the position of the center-of-gravity of said left pedal and said right pedal is correct.

2. The gait training machine as claimed in claim 1, wherein said gait judgment unit calculates the number of passes, the number of times of steering, the number of times that meet a first condition which indicates that the position of the center-of-gravity of said left pedal and said right pedal is correct, and the number of times that meet a second condition which indicates that the user's left foot and the right foot's ankle movement are correct; when said gait judgment unit receives said passing signal, the number of passes is increased by one, and said gait determining logic is used to determine whether the bearing weight of said left pedal and said right pedal is correct, if correct, the number of times that meet said first condition is increased by one, if not, the number of times that meet said first condition is unchanged; when said gait judgment unit receives said steering signal, the number of times of steering is increased by one, and said gait determining logic is also used to determine whether the user's left foot and the right foot's ankle movement are correct, if correct, the number of times that meet said second condition is increased by one, if not, the number of times that meet said second condition remains unchanged.

3. The gait training machine as claimed in claim 2, further comprising an evaluation module disposed at said controller, said evaluation module comprising a guiding unit; after said guiding unit receives said steering signal generated by said driving circuit, said guiding unit transmits a first guiding indicator to guide the user to move the center-of-gravity to one of the feet; after said guiding unit receives said steering signal again, said guiding unit transmits a second guiding indicator to guide the user to move the center-of-gravity to the other foot.

4. The gait training machine as claimed in claim 3, wherein said evaluation module further comprises a level-of-involvement evaluation unit that calculates an ankle joint correct rate and a center-of-gravity correct rate, the ankle joint correct rate=the number of times that meet said second condition/the number of times of steering*100%, the center-of-gravity correct rate=the number of times that meet said first condition/the number of passes*100%.

5. A method of using a gait training machine, which is characteristic in that said gait training machine comprising a base, a driving module, a sensor module, a controller, a touch screen, a signal processing module and an evaluation module, said driving module comprising a driving circuit, a motor and two moving platforms, said sensor module comprising a left pedal, a right pedal, a plurality of pressure sensors and a position sensor, said left pedal and said right pedal being respectively pivotally connected to said moving platforms, said motor driving said moving platforms to move said left pedal and said right pedal in the opposite direction, said pressure sensors being respectively mounted on corners of said left pedal and said right pedal, said position sensor being disposed in said base, said touch screen being adapted for the user to input data and to display information, said controller being electrically connected to said driving circuit, each said pressure sensor, said position sensor and said touch screen, said signal processing module being disposed in said controller and comprising a gait detecting unit and a gait judgment unit, said gait determining unit storing a center-of-gravity calculation logic and a gait determining logic, said evaluation module being disposed in said controller and comprising a guiding unit, the method of using said gait training machine comprising the steps of:

A) preparation stage: where the user puts the both feet on said left pedal and said right pedal respectively, and said touch screen is for the user to set a speed level, a step distance, and a training time;

B) gait training machine action stage: where said controller converts said speed level, said step length and said training time into a driving data, and outputs said driving data to said driving circuit of said driving module for said driving circuit to control the rotation of said motor, thereby controlling the movement speed, the movement time and the range of motion of each of said moving platforms to drive said left pedal and said right pedal; the range of motion of each said moving platform is limited to said step length; at the reciprocating turning point of each said moving platform, said motor produces a reverse rotation, at this time, said driving circuit generates a steering signal; when said left pedal and said right pedal move with the respective said moving platforms to pass said position sensor, said position sensor generates a passing signal;

C) signal detection and judgment: where said gait detecting unit receives a weight signal from each said pressure sensor, said passing signal measured by said position sensor and said steering signal from said driving circuit, said gait judgment unit receives each weight signal from said gait detecting unit, said passing signal and said steering signal and uses said center-of-gravity calculation logic to calculate the bearing weight of said left pedal and said right pedal and the center-of-gravity position on said left pedal and said right pedal and also uses said gait determining logic to determine whether the bearing weight of said eft pedal and said right pedal is correct and whether the center-of-gravity position is correct; said gait judgment unit calculates the number of passes, the number of times of steering, the number of times that meet a first condition which indicates that the position of the center-of-gravity of said left pedal and said right pedal is correct and the number of times that meet a second condition which indicates that the user's left foot and the right foot's ankle movement are correct; when said gait judgment unit receives said passing signal, said number of passes is increased by one, and said gait determining logic is used to determine whether the bearing weight of said left pedal and said right pedal is correct, if correct, said number of times that meet said first condition is increased by one, and if not, said number of times that meet said first condition is unchanged; when said gait judgment unit receives said steering signal, said number of times of steering is increased by one, and said gait determining logic is used to determine whether the user's left foot and the right foot's ankle movement are correct, if all are correct, then said number of times that meet said second condition is increased by one, and if not, said number of times that meet said second condition is unchanged;

D) guiding display: after receiving said steering signal from said driving circuit in the process that said left pedal moves forward and said right pedal moves backward, said guiding unit transmits a left guiding signal to said touch screen, at this time, said touch screen displays a left arrow for guiding the user to move the center-of-gravity to the left foot, then, after receiving said steering signal again, said guiding unit transmits a right guiding signal to said touch screen, at this time, said touch screen displays a right arrow for guiding the user to move the center-of-gravity to the right foot; in addition, said guiding unit also receives from said gait judgment unit the result of determining whether the user's left and right ankle movements are correct, and said touch screen displays a left-shoe icon, a right-shoe icon, if the left ankle joint moves correctly, a left ankle joint display signal is sent to said touch screen, and said left-shoe icon is colored or illuminated after receiving the left ankle joint display signal for the user to understand that the left ankle joint moves correctly, if the right ankle joint moves correctly, a right ankle joint display signal is sent to said touch screen, and said right-shoe icon is colored or illuminated after receiving the right ankle joint display signal for the user to understand that the right ankle joint moves correctly; and E) repeated action: where steps B)-D) are repeated till said training time is ended.

6. The method of claim 5, wherein said evaluation module further comprises a level-of-involvement evaluation unit, the method further comprises step F) after step E), in step F) result display: said level-of-involvement evaluation unit calculates an ankle joint correct rate and a center-of-gravity correct rate within the training time, the ankle joint correct rate=the number of times that meet said second condition/the number of times of steering*100%, the center-of-gravity correct rate=the number of times that meet said first condition/the number of passes*100%; said touch screen is able to be set to display the number of times that meet said second condition, the number of times of steering, the ankle joint correct rate, the number of times that meet said first condition, the number of passes, or the center-of-gravity correct rate.

7. The method as claimed in claim 5, wherein said gait determining logic is introduced to be:

said gait judgment unit pre-stores a first threshold and a second threshold;

with respect to the center-of-gravity position of the user on said left pedal, the moving direction of said left pedal and said right pedal is the front-rear direction, and when the user stands on said left pedal and said right pedal, the side the user faces is the front side, Total LValue: left pedal bearing weight;

Total RValue: right pedal bearing weight;

Total Value: the user's weight;

Total Value=Total $L$Value+Total $R$Value;

when said left pedal moves backward and said passing signal is received, Total LValue/Total Value≥said first threshold, it is determined that the user's body center-of-gravity is on the left foot, and the bearing weight of said left pedal is correct, if not, an error of the bearing weight of said left pedal is determined;

when said right pedal moves backward and said passing signal is received, Total RValue/Total Value≥said first threshold, it is determined that the user's body center-of-gravity is on the right foot, and the bearing weight of said right pedal is correct, if not, an error of the bearing weight of said right pedal is determined;

define the forward moving direction of said left pedal and said right pedal as the X direction and the outward direction perpendicular to the X direction as the Y direction;

when |LX_Position|/(LX_Proportion/2)≥said second threshold, it indicates that the left ankle joint movement is correct, if not, it indicates that the left ankle joint movement is wrong;

LX_Position: the coordinate value of the center-of-gravity of said X direction on said left pedal;

LX_Proportion: the length of said left pedal along said X direction with the geometric center of said left pedal as the origin;

when |RX_Position|/(RX_Proportion/2)≥said second threshold, it indicates that the right ankle joint movement is correct, if not, it indicates that the right ankle joint movement is wrong;

RX Position: the coordinate value of the center-of-gravity of said X direction on said right pedal;

RX_Proportion: the length of said right pedal along said X direction with the geometric center of said right pedal as the origin.

8. The method as claimed in claim 7, wherein the number of said pressure sensors is eight, which are respectively arranged in the four corners of said left pedal and said right pedal, and the said pressure sensors on the left rear side, left front side, right front side and right rear side of said left pedal are defined as sensor A, sensor B, sensor C and sensor D respectively and the said pressure sensors on the right rear side, right front side, left front side and left rear side of said right pedal are defined as sensor E, sensor F, sensor G and sensor H respectively; when the user stands on said left pedal and said right pedal, the weight is applied to said left pedal and said right pedal;

Total $L$Value=$L$Value1+$L$Value2+$L$Value3+$L$Value4;

Total LValue: left pedal bearing weight;
LValue1: the weight signal detected by said sensor A;
LValue2: the weight signal detected by said sensor B;
LValue3: the weight signal detected by said sensor C;
LValue4: the weight signal detected by said sensor D;

Total $R$Value=$R$Value1+$R$Value2+$R$Value3+$R$Value4;

Total RValue: right pedal bearing weight;
RValue1: the weight signal detected by said sensor E;
RValue2: the weight signal detected by said sensor F;
RValue3: the weight signal detected by said sensor G;
RValue4: the weight signal detected by said sensor H;

Total Value=Total $L$Value+Total $R$Value;

Total Value: the user's weight;
then the center-of-gravity position on said left pedal is obtained by the following relationship:

$LX$_Gravity=(($L$Value3+$L$Value2)*$LX$_Proportion)/ Total $L$Value;

$LY$_Gravity=(($L$Value2+$L$Value1)*$LY$_Proportion)/ Total $L$Value;

LValue1: the weight signal detected by said sensor A;
LValue2: the weight signal detected by said sensor B;
LValue3: the weight signal detected by said sensor C;
LX_Proportion=the length of said left pedal along said X direction with the geometric center of said left pedal as the origin;
LY_Proportion=the length of said left pedal along said Y direction with the geometric center of said left pedal as the origin;
Thus, the center-of-gravity coordinates on said left pedal (LX_Position, LY_Position) is obtained by the following relationship:

$LX$_Position=$LX$_Gravity−($LX$_Proportion/2);

$LY$_Position=$LY$_Gravity−($LY$_Proportion/2);

the center-of-gravity position on said right pedal is obtained by the following relationship:

$RX$_Gravity=(($R$Value3+$R$Value2)*$RX$_Proportion)/ Total $R$Value;

$RY$_Gravity=(($R$Value2+$R$Value1)*$LY$_Proportion)/ Total $R$Value;

RValue1: the weight signal detected by said sensor E;
RValue2: the weight signal detected by said sensor F;
RValue3: the weight signal detected by said sensor G;
RX_Proportion: the length of said right pedal along said X direction with the geometric center of said right pedal as the origin;
RY_Proportion: the length of said right pedal along said Y direction with the geometric center of said right pedal as the origin;
the center-of-gravity coordinates on said right pedal (RX_Position, RY_Position) is obtained by the following relationship:

$RX$_Position=$RX$_Gravity−($RX$_Proportion/2);

$RY$_Position=$RY$_Gravity−($RY$_Proportion/2).

9. The method as claimed in claim 7, wherein said first threshold is 0.8; said second threshold is 0.8.

10. The method as claimed in claim 5, wherein in the step D) guiding display, said left-shoe icon comprises a left-heel portion and a left-sole portion, and said right-shoe icon comprises a right-heel portion and a right-sole portion; when said guiding unit receives said steering signal during the process that said left pedal moves forward and said right pedal moves backward, said guiding unit transmits a first display signal to said touch screen, at this time, said left-heel portion is colored or illuminated to guide the user to put the center-of-gravity of the left foot on the left heel and also said right-sole portion is colored or illuminated to guide the user to put the center-of-gravity of the right foot on the right sole; then, said left pedal moves backward and said right pedal moves forward; when said guiding unit receives said passing signal, said guiding unit transmits a second display signal to said touch screen, at this time, said left-sole portion is colored or illuminated to guide the user to put the center-of-gravity of the left foot on the left sole and also said right-heel portion is colored or illuminated to guide the user to put the center-of-gravity of the right foot on the right heel.

* * * * *